United States Patent [19]

Heidmueller

[11] Patent Number: 5,320,632
[45] Date of Patent: Jun. 14, 1994

[54] SURGICAL SUTURING APPARATUS

[75] Inventor: Elke Heidmueller, Cologne, Fed. Rep. of Germany

[73] Assignee: Harald Heidmueller, Fed. Rep. of Germany

[21] Appl. No.: 974,119

[22] Filed: Nov. 10, 1992

[30] Foreign Application Priority Data

Nov. 13, 1991 [DE] Fed. Rep. of Germany ....... 4137218

[51] Int. Cl.⁵ ............................................. A61B 17/04
[52] U.S. Cl. ..................................... 606/144; 112/169
[58] Field of Search ............... 606/139, 144, 145, 147, 606/148, 151, 184, 185, 186, 187; 112/169, 80.03

[56] References Cited

U.S. PATENT DOCUMENTS 4,493,323 1/1985 Albright et al. ................... 606/144

FOREIGN PATENT DOCUMENTS 812579 5/1937 France ................................ 606/144
1093329 5/1984 U.S.S.R. ............................. 606/145

Primary Examiner—Tamara L. Graysay
Attorney, Agent, or Firm—Diller, Ramik & Wight

[57] ABSTRACT

For sewing up a surgical opening (32), an instrument (10) is provided to be introduced thereinto. Needle holders (19), having needles (25) attached thereon, are laterally extended out of the instrument (10). By raising the instrument (10), the needles (25) are pierced through the cutaneous tissue (33) from the inside to the outside while the thread (30) passing through the needles (25) forms a loop within the patient's body. A needle catcher (26) is used for withdrawing the needles (25) out of the patient's body, the needles (25) being released from the needle holders (19). Finally, the thread loop can be tied into a knot above the surgical opening (32) outside the patient's body.

6 Claims, 6 Drawing Sheets

SURGICAL SUTURING APPARATUS

BACKGROUND OF THE INVENTION

The invention is directed to a surgical suturing apparatus for closing an operation wound or a stab incision by at least one thread.

A known surgical suturing apparatus according to U.S. Pat. No. 4,493,323 comprises an instrument with a longitudinal housing of oval cross section wherein two parallel needle holders are displaceable in lengthwise direction. Each of the needle holders is adapted to have a needle inserted therein in such a manner that the two needles protrude towards the patient-side end. The surgical thread is pulled through the rear ends of the needles so as to form a wide loop. When the instrument is used, it is introduced by a piercing tool into the body or the knee of the patient, and the needles are advanced while laterally enclosing the area which is to be sutured. Then, the needles are pushed further on until emerging again from the patient's body on the opposite side. There, the ends of the thread can be seized and tied into a knot above the skin. This suturing apparatus makes it necessary that the needles are pierced completely through the body, i.e. that they will emerge again on the end opposite the puncturing end. The known apparatus is not suited for sewing up stab incisions which are accessible only from one side.

In surgical operations, e.g. in the abdominal and thorax regions, the surgical wound is closed by suturing with surgical suture material. In relatively long surgical incisions, application of a surgical suture normally does not cause any major problems. However, difficulties will occur in stab incisions, particularly in the region of the abdomen and the thorax. If the surgical incision is so short that the suture can be sewed only by at least one loop of the thread, the surgeon will have difficulties to guide the needle with the needle holder under the skin and to pierce it through the abdominal wall from below since he cannot reach through the incision opening with his fingers.

SUMMARY OF THE INVENTION

It is an object of the invention to provide a surgical suturing apparatus which is adapted for sewing up stab incisions without the need for the surgeon to grip through the incision region into the patient's body with his fingers or known surgical instruments.

The surgical suturing apparatus according to the invention comprises an instrument having its lower end provided with at least two needle holders whereon surgical needles can be mounted with their tips pointing upwards. The instrument is introduced into the surgical wound and then is retracted, with the needles being arranged at a lateral distance from the instrument. In doing so, the upwardly directed needle tips simultaneously penetrate the edges of the tissue layers to be sutured. A thread of suture material, guided through holes formed within the needles, forms a loop or snare within the patient's body while both of the thread ends are moved out of the patient's body through the needles. Then, the thread ends can be seized and the thread can be tied and knotted from the outside for thus closing the surgical wound.

The surgical suturing apparatus of the invention is adapted for sewing up two edges of a wound by generating a closed thread loop in a single working step while the surgeon does not have to grip with his fingers into the patient's body. When the needles have pierced, the to-be-sutured tissue of the patient from the inside to the outside, they are seized and withdrawn from the needle holders whereon they have been held by clamping action. The instrument is handled in such a manner that the needles, possibly after having pierced the tissue of the skin from the inside to the outside, are retracted on the outside and are slipped off over the free thread ends. Instead of using a needle catcher, the needles can also be seized by hand or some other instrument.

A particular advantage resides in the simple handling of the suturing apparatus which does not require any special skill or deeper experience in the sewing of surgical wounds. The instrument is merely introduced into the surgical wound. Then, if required, the needle holders are e.g. laterally displaced for arranging the needles at a distance from the wall of the rod of the instrument. Then, the rod is retracted by a distance while the needles penetrate the tissue in the vicinity of the edges of the wound. Subsequently, the needles can be seized by the needle catcher or by hand or another instrument and be withdrawn from the patient's body. Thereafter, the suturing apparatus is pulled out of the patient's body and finally the thread loop is knotted outside the patient's body.

In a preferred embodiment of the suturing apparatus, the needle holders are guided to be moved transversely to the instrument, an operating mechanism for lateral movement of the needle holders extending along the rod-shaped instrument. This embodiment offers the advantage that, in the inserted condition of the small instrument, the needles are in close abutment thereon or are sunk into the outer contour of the instrument and do not protrude. Only when the needles are in a position below the tissue to be sewed, the needle holders are laterally extended by the operating mechanism. However, it is also possible to fixedly attach the needle holders at a certain distance from the instrument; in this case, the instrument has to be turned by about 90° after penetration into the surgical wound so that the needles are moved into the area of the lateral edges of the surgical wound. In further accordance with the invention a frustoconical needle catcher is provided for displacing, if required, skin and fatty tissue and thus allows sewing to be performed only on the fascia and the peritoneum.

Embodiments of the invention will be explained in greater detail hereunder with reference to the drawings.

DESCRIPTION OF THE PREFERRED EMBODIMENTS

Figure 1:
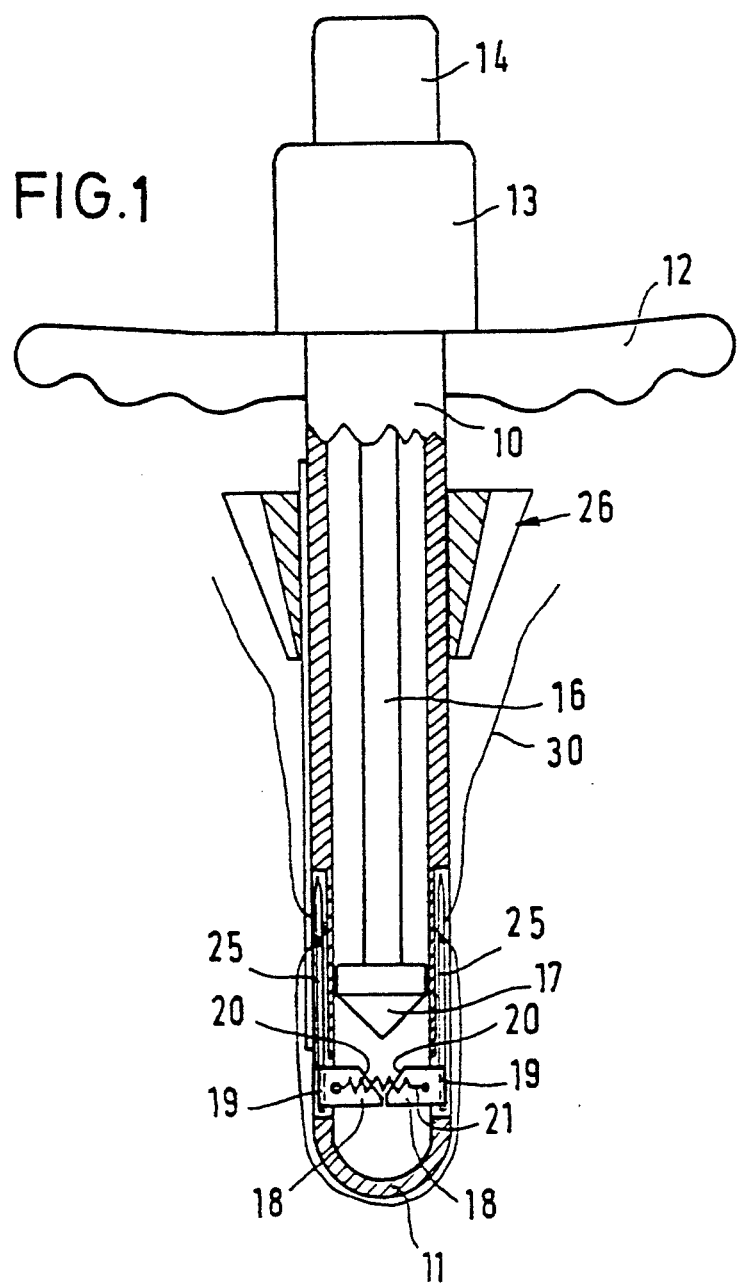
FIG. 1 shows a partially sectional side view of the suturing apparatus in the inoperative condition during insertion of the rod into the patient's body.

The apparatus shown in FIGS. 1-5 comprises an elongate instrument 10 shaped as a linear hollow rod which in the current example is configured as a tube, with the front end 11 of the tube being closed by a rounded dome. On the rear end of instrument 10, a handle 12 is arranged for the maneuvering of instrument 10. Handle 12 has a guide portion 13 arranged thereon, wherein an operating button 14 can be displaced and which contains a spring 15 for biasing the operating button 14 towards the outside. Operating button 14 is connected to a bar 16 extending within the hollow rod and having its lower end provided with an operating head or cam means 17.

Figure 2:
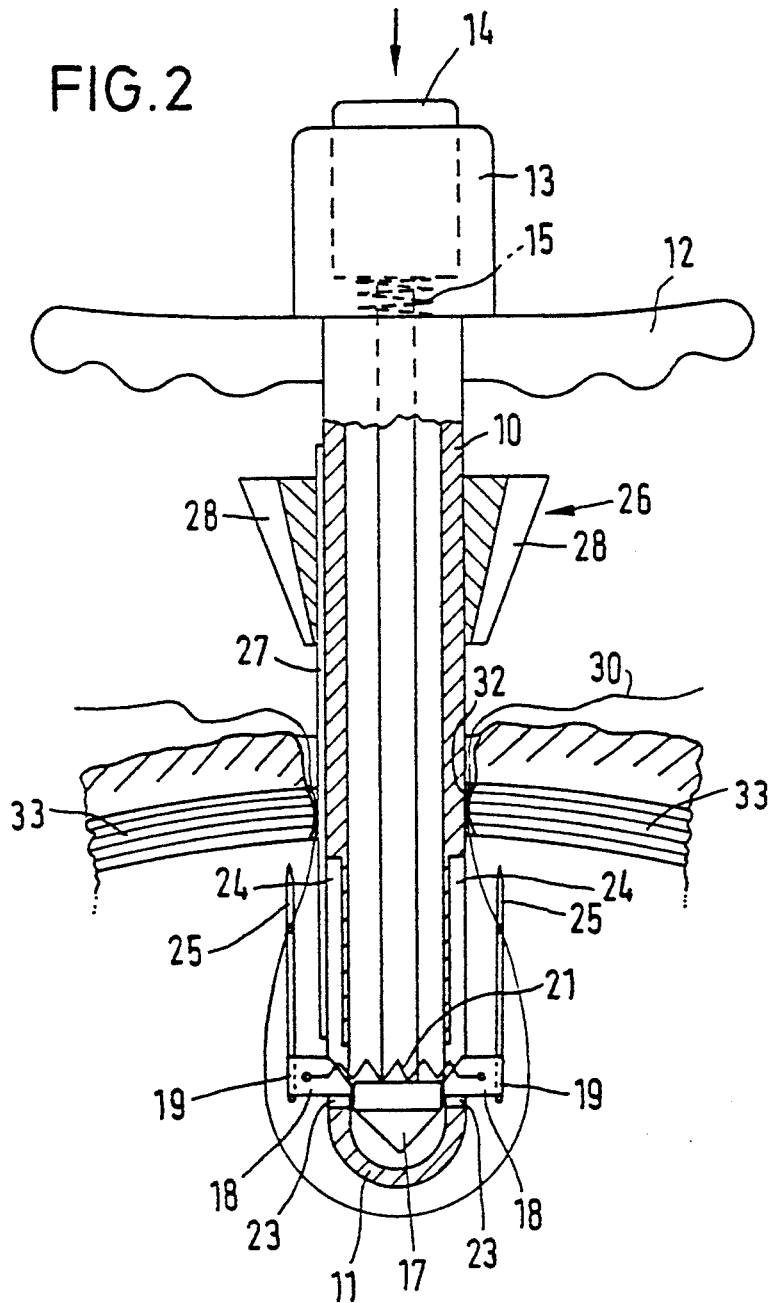
FIG. 2 illustrates the lateral movement of the needle holders from the rod by the operating mechanism.

On the lower end of the rod, there are provided two sliding portions 18 which are guided transversely to the longitudinal direction of the rod. Each of said sliding portions 18 comprises a needle holder 19. The sliding portions 18 have their confronting ends provided with oblique surfaces or cam follower means 20 formed a V-shaped gap within instrument 10. The wedge-shaped operating head or cam means 17 can penetrate into this gap for moving the sliding portions 18 apart from each other in lateral direction by acting against the cam follower means 20. A spring means 21 serves for tensioning the sliding portions 18 in such a manner that they are withdrawn into instrument 10. When the operating button 14 is pushed so that the operating head 17 drives the sliding portions 18 apart, the needle holders 19 are moved laterally out of instrument 10 as shown in FIG. 2. Control of the two needle holders 19 by operating head 17 is performed synchronously, i.e. both of the needle holders 19 are moved symmetrically to each other with respect to the axis of the rod.

The sliding portions 18 project through holes 23 of the rod wall. Above each of said holes 23, there is arranged a lengthwise groove 24 on the outer side of instrument 10. These grooves 24 serve for receiving the needles 25 in the condition shown in FIG. 1.

The needle catcher 26 is displaceable along instrument 10. A bar 27 extending in longitudinal direction on rod 10 and entering into a corresponding groove of needle catcher 26, precludes twisting of needle catcher 26 relative to instrument 10. Needle catcher 26 has frustoconical shape, widening in upward direction (away from end 11). On two opposite sides, needle catcher 26 has clamping slits 28 formed therein whose bottom can be configured corresponding to the orientation and the angle of the conicity of needle catcher 26 and in which the needles 25 can be clamped tight. Instead of the clamping slits 28, it is also possible to use other clamping means suited for penetration of the needle tips thereinto, and primarily those which allow unhindered penetration of the needles but permit a withdrawal thereof only upon actuation of a handle.

The needles 25 are inserted in needle holder 19 with their blunt lower ends while their tips are pointing upwardly. Substantially in the intermediate region of the length of the needle, there is provided a respective needle eye through which the thread 30 can be pulled. The needles can also be arranged obliquely to instrument 10.

When using the suturing apparatus, the thread 30 extends through the eyes of both needles 25 so that the two thread ends freely protrude in upward direction. The needles 25 are laterally withdrawn into instrument 10 or pulled thereagainst. In the condition shown in FIG. 1, the suturing apparatus is introduced into the patient's body by stab incision.

FIG. 2 shows the cut opening 32 of the stab incision and the adjacent tissue 33. As known in the field, this tissue 33 consists of several layers, i.e. the peritoneum, the fascial tissue and the overlaying fatty and cutaneous tissue.

Figure 3:
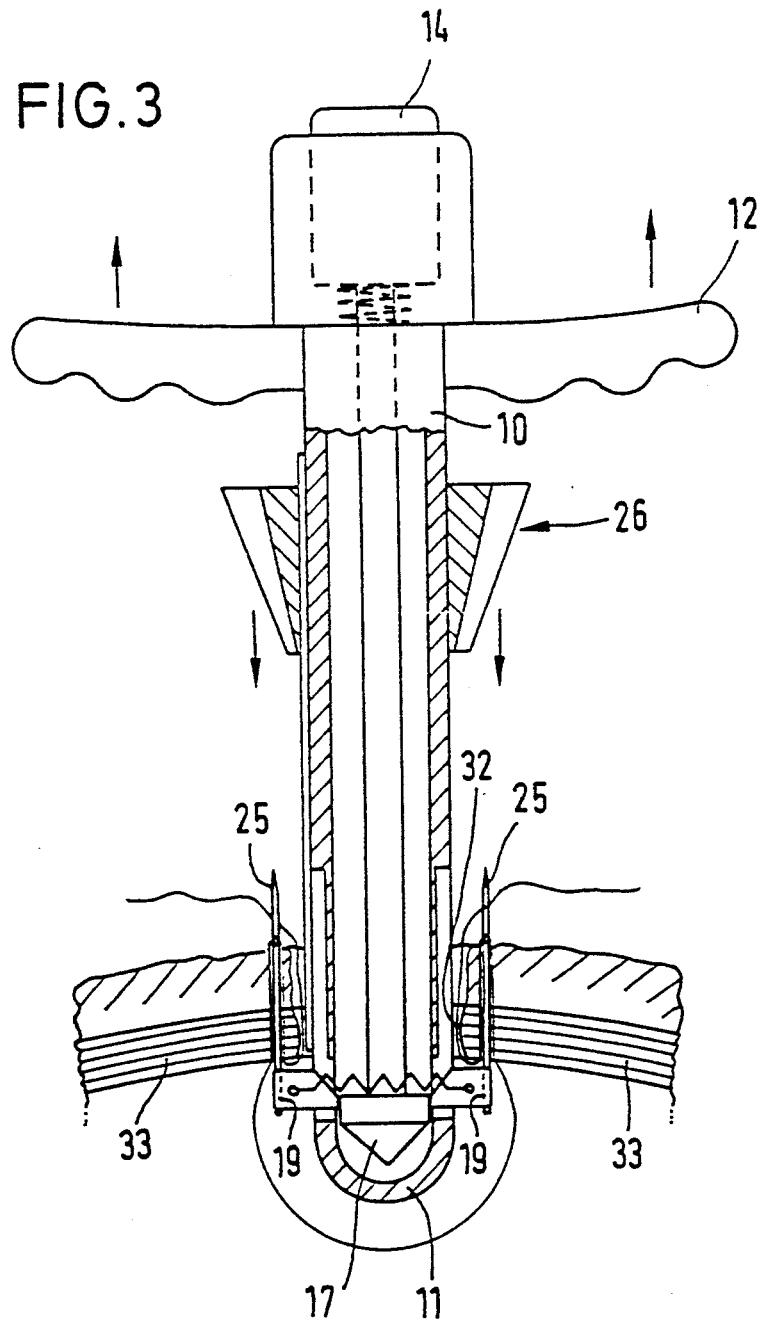
FIG. 3 illustrates the perforation of the tissue from the inside.
Figure 4:
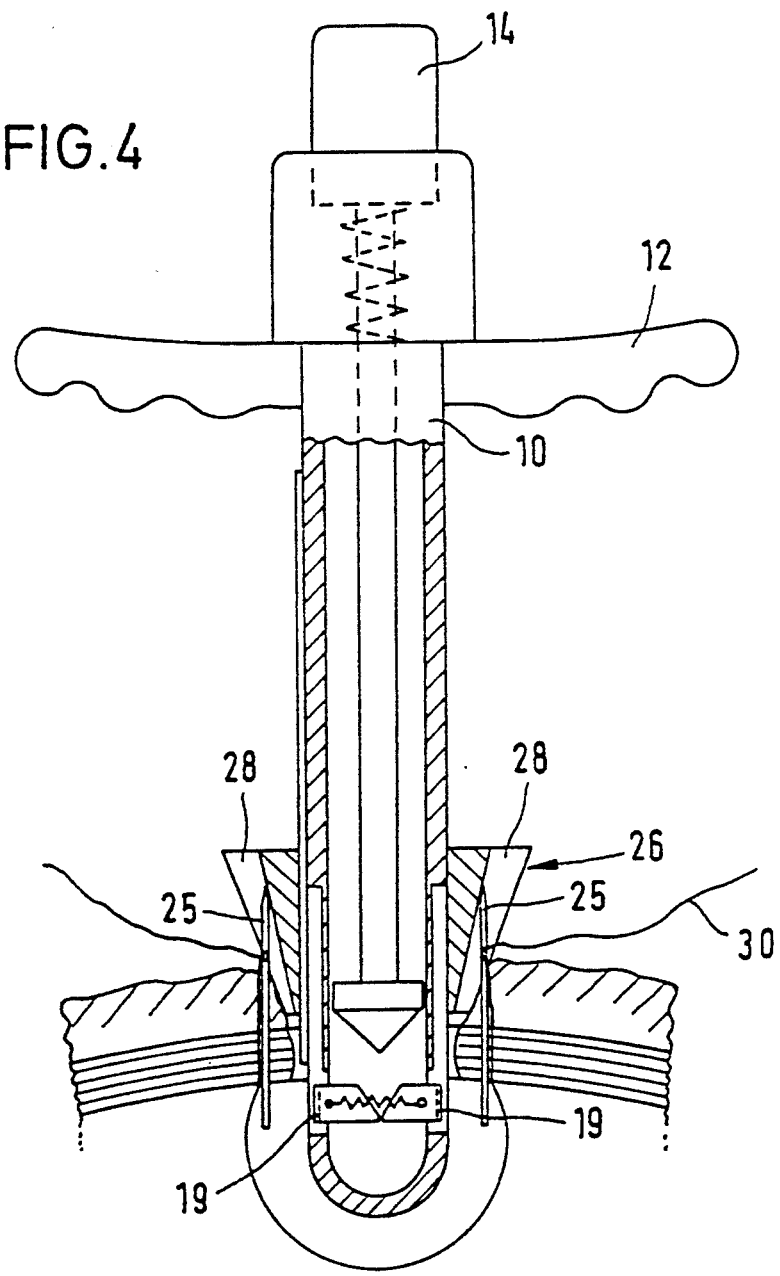
FIG. 4 illustrates the insertion of the needle catcher for holding the needle tips from the outside.

By pressing the operating button 14, the needle holders 19 are moved laterally out of instrument 10 as shown in FIG. 2. By a locking mechanism (not shown), the operating button 14 can be arrested in this position so that there is no need to further keep it pressed by hand. Then, instrument 10 is pulled up on handle 12 as shown in FIG. 3, the needles 25 with their tips penetrating the edge of the body opening 32 from the inside to the outside, so that the needle tips project out of the tissue to be sewed. Now, as evident from FIG. 4, needle catcher 26 is moved by the surgeon along instrument 10 in downward direction until the tips of the needles enter into the clamping slits 28 and are retained by them. In this condition, the needle catcher 26 can be pulled up while taking the needles 25 along with it, the needles being released from the needle holders 19. This is effected because the needle catcher 26 can hold the needles more tightly than the needle holders 19 can do. However, it is also possible to first retract the needle holders 19 according to FIG. 4 so that these become detached from the needles 25, and only then move up the needle catcher 26 along instrument 10. Due to the conical shape of needle catcher 26, the skin and the fatty tissue are pushed aside and the needle tips are seized by needle catcher 26 above the fascial tissue.

Figure 5:
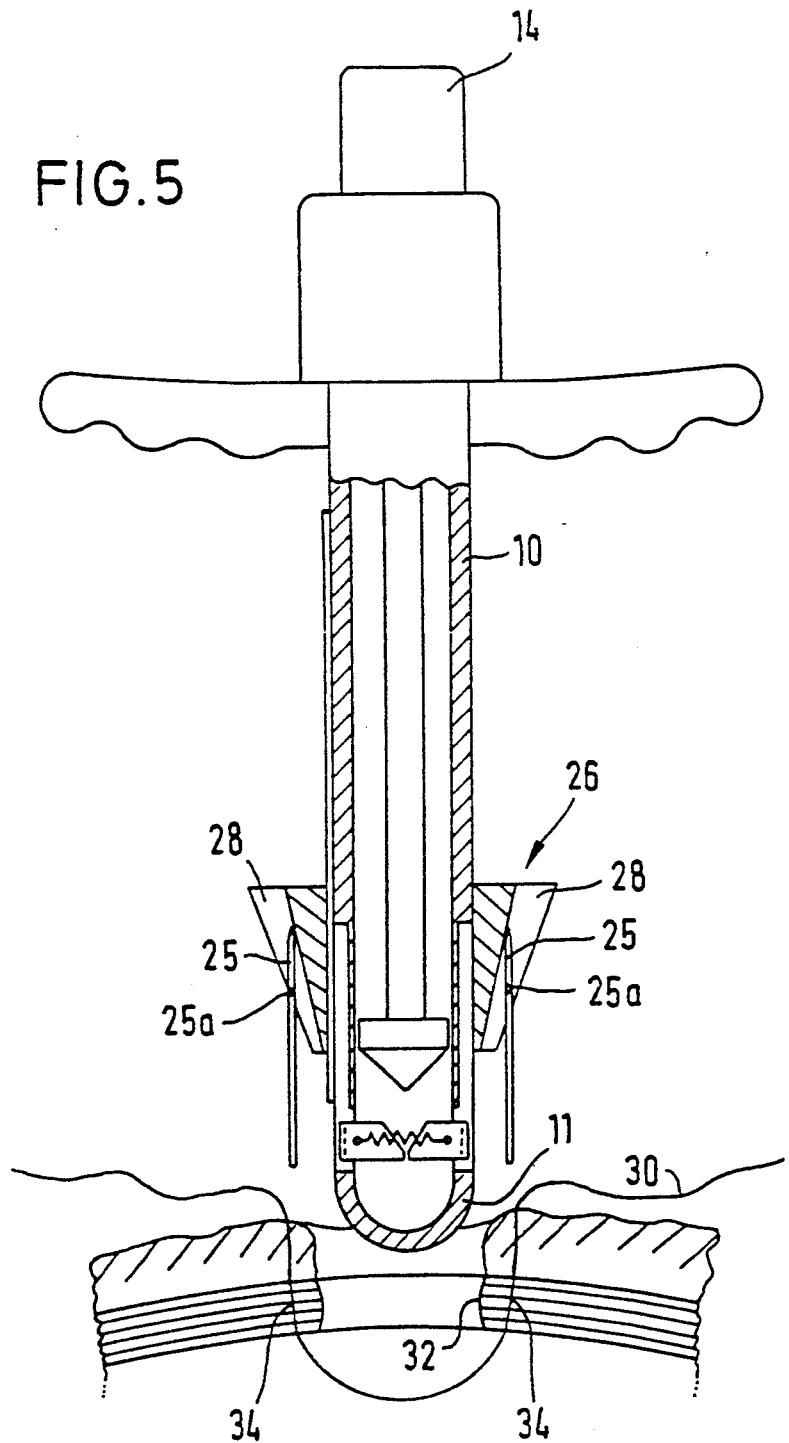
FIG. 5 illustrates the withdrawal of the apparatus from the patient's body.

FIG. 5 shows the condition wherein the needles 25 are arrested on needle catcher 26 and are pulled out of the stab incision 32 together with needle catcher 26 and instrument 10. During this movement, a respective portion of thread 30 slides through the respective needle eye 25a of the associated needle 25 so that the needles finally become free of thread 30. The thread 30, which now has been guided through the two puncture channels 34 on both sides of the surgical opening 32 and forms a loop under the surgical opening, can now be tied into a knot above the surgical opening 32 while the surgical opening is contracted.

Figures 6, 7:
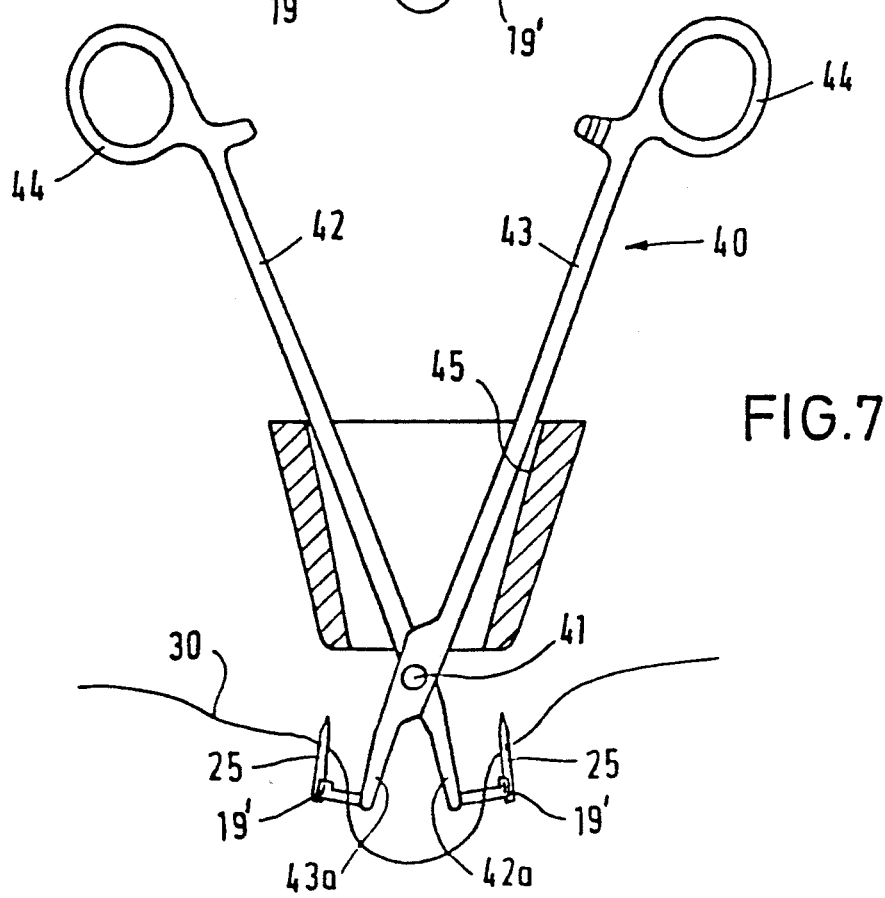
FIG. 6 shows a second embodiment of the apparatus in the folded insertion condition.
FIG. 7 shows the apparatus of FIG. 6 in the unfolded condition.

In the embodiment according to FIGS. 6 and 7, the instrument 40 comprises a forceps means having two forceps legs 42,43 crossing each other in a joint 41. The forceps legs 42,43 have their long grip legs provided with grip portions 44 and have their short operating legs 42a or 43a provided with needle holders 19' directed outwardly, i.e. oppositely, and protruding at right angles from the operating legs. Into these needle holders 19', the needles 25 are, clampingly inserted, their tips being directed toward the grip portions 44. The forceps legs 42,43 run through a needle catcher 26 which comprises a corresponding slit-shaped lengthwise channel 45 and is displaceable along instrument 40.

Instrument 40 is introduced into the surgical opening of the body in the condition shown in FIG. 6. Then, the forceps legs 42,43 are moved apart so that the mutual distance of the needles 25 becomes larger. In this condition, which is illustrated in FIG. 7, the instrument 40 is pulled up while the needles 25 penetrate the body tissue. Then, by advancing the needle catcher 26, the needle tips projecting out from the skin are seized by needle catcher 26 and the needles are withdrawn from the needle holders 19'. Finally, the instrument 40, with its grip legs and operating legs abutting each other, is pulled out of the surgical wound, and then the suture material thread 30 is knotted outside the patient's body for thus closing the surgical wound.

What is claimed is:

1. A surgical suturing apparatus comprising a relatively elongated instrument (10, 40) having generally opposite spaced first and second end portions (generally 11, 13; 42a,43a, 44), means (19) located at said first end portion (11; 42a 43a) for removably supporting needles (25) at said first end portion (11; 42a, 43a) with tips of said needles directed toward said second end portion (13, 44,), and means (18, 18) for mounting said needles for reciprocal sliding movement relative to each other.

2. A surgical suturing apparatus comprising a relatively elongated instrument (10, 40) having generally opposite spaced first and second end portions (generally 11, 13; 42a,43a, 44) means (19) located at said first end portion (11; 42a 43a) for removably supported needles (25) at said first end portion (11; 42a, 43a) with tips of said needles directed toward said second end portion (13, 44,), means (18, 18) for mounting said needles for reciprocal sliding movement relative to each other, and means (18, 23) for guiding said needles during the reciprocal sliding movement therebetween.

3. A surgical suturing apparatus comprising a relatively elongated instrument (10, 40) having generally opposite spaced first and second end portions (generally 11, 13; 42a,43a, 44), means (19) located at said first end portion (11; 42a 43a) for removably supporting needles (25) at said first end portion (11; 42a, 43a) with tips of said needles directed toward said second end portion (13, 44,), and means (26) disposed between said elongated instrument first and second end portions for clampingly gripping the needle tips.

4. A surgical suturing apparatus comprising a relatively elongated instrument (10, 40) having generally opposite spaced first and second end portions (generally 11, 13; 42a,43a, 44), means (19) located at said first end portion (11; 42a 43a) for removably supporting needles (25) at said first end portion (11; 42a, 43a) with tips of said needles directed toward said second end portion (13, 44), means (17, 20; 41) for displacing needle tips from a first relatively close body opening insertion position (FIGS. 1 and 6) to a second relatively more remote skin penetration position (FIGS. 2 and 7) to effect respective introduction of the needles within a body opening and subsequent needle penetration into the skin contiguous thereto, and means (18, 18) for mounting said needles for reciprocal sliding movement relative to each other.

5. A surgical suturing apparatus comprising a relatively elongated instrument (10, 40) having generally opposite spaced first and second end portions (generally 11, 13; 42a,43a, 44), means (19) located at said first end portion (11; 42a 43a) for removably supporting needles (25) at said first end portion (11; 42a, 43a) with tips of said needles directed toward said second end portion (13, 44,), means (17, 20; 41) for displacing needle tips from a first relatively close body opening insertion position (FIGS. 1 and 6) to a second relatively more remove skin penetration position (FIGS. 2 and 7) to effect respective introduction of the needles within a body opening and subsequent needle penetration into the skin contiguous thereto, means (18, 18) for mounting said needles for reciprocal sliding movement relative to each other, and means (18, 23) for guiding said needles during the reciprocal sliding movement therebetween.

6. A surgical suturing apparatus comprising a relatively elongated instrument (10, 40) having generally opposite spaced first and second end portions (generally 11, 13; 42a,43a, 44), means (19) located at said first end portion (11; 42a 43a) for removably supporting needles (25) at said first end portion (11; 42a, 43a) with tips of said needles directed toward said second end portion (13, 44,), means (17, 20; 41) for displacing needle tips from a first relatively close body opening insertion position (FIGS. 1 and 6) to a second relatively more remote skin penetration position (FIGS. 2 and 7) to effect respective introduction of the needles within a body opening and subsequent needle penetration into the skin contiguous thereto, and means (26) disposed between said elongated instrument first and second end portions for clampingly gripping the needle tips.

* * * * *